United States Patent
Frid

(10) Patent No.: US 8,353,951 B2
(45) Date of Patent: Jan. 15, 2013

(54) RADIO-OPAQUE ENDOPROSTHESIS

(75) Inventor: Noureddine Frid, B-Beersel (BE)

(73) Assignee: Cardiatis S.A., Isnes (BE)

( * ) Notice: Subject to any disclaimer, the term of this patent is extended or adjusted under 35 U.S.C. 154(b) by 361 days.

(21) Appl. No.: 12/093,019

(22) PCT Filed: Oct. 2, 2006

(86) PCT No.: PCT/EP2006/066951
§ 371 (c)(1),
(2), (4) Date: Jan. 21, 2009

(87) PCT Pub. No.: WO2007/039587
PCT Pub. Date: Apr. 12, 2007

(65) Prior Publication Data
US 2009/0192587 A1  Jul. 30, 2009

(30) Foreign Application Priority Data

Oct. 3, 2005  (EP) .................................... 05109136

(51) Int. Cl.
*A61F 2/06* (2006.01)
(52) U.S. Cl. ...................... 623/1.34; 623/1.44; 623/1.15
(58) Field of Classification Search ................ 623/1.15, 623/1.36, 1.42, 1.44, 1.46, 1.22, 1.34, 1.35
See application file for complete search history.

(56) References Cited

U.S. PATENT DOCUMENTS

| 4,922,905 A | 5/1990 | Strecker | |
|---|---|---|---|
| 6,287,331 B1 * | 9/2001 | Heath | 623/1.15 |
| 6,569,194 B1 | 5/2003 | Pelton | |
| 2002/0082683 A1 * | 6/2002 | Stinson et al. | 623/1.23 |
| 2003/0121148 A1 | 7/2003 | DiCaprio | |
| 2003/0139799 A1 | 7/2003 | Ley et al. | |
| 2004/0111149 A1 * | 6/2004 | Stinson | 623/1.34 |
| 2004/0215332 A1 * | 10/2004 | Frid | 623/1.22 |
| 2005/0154445 A1 * | 7/2005 | Hunter et al. | 623/1.13 |
| 2006/0004440 A1 * | 1/2006 | Stinson | 623/1.34 |
| 2006/0106451 A1 * | 5/2006 | Busiashvili | 623/1.15 |
| 2006/0116752 A1 * | 6/2006 | Norton et al. | 623/1.34 |
| 2006/0142851 A1 * | 6/2006 | Molaei et al. | 623/1.44 |
| 2008/0221670 A1 * | 9/2008 | Clerc et al. | 623/1.34 |
| 2008/0300673 A1 * | 12/2008 | Clerc et al. | 623/1.15 |
| 2009/0177268 A1 * | 7/2009 | Lundkvist et al. | 623/1.22 |
| 2010/0070025 A1 * | 3/2010 | Heath | 623/1.34 |
| 2010/0152837 A1 * | 6/2010 | Lundkvist et al. | 623/1.22 |

FOREIGN PATENT DOCUMENTS

| EP | 0 804 909 A | 11/1997 |
|---|---|---|
| EP | 0 809 998 A2 | 12/1997 |
| EP | 0894481 A2 | 2/1999 |
| EP | 0 938 878 A2 | 9/1999 |
| WO | WO 93/19804 A | 10/1993 |
| WO | WO 94/01056 A | 1/1994 |
| WO | WO 02/47579 A | 6/2002 |
| WO | WO 02/47579 A1 | 6/2002 |
| WO | WO 2005/028014 A1 | 3/2005 |

* cited by examiner

*Primary Examiner* — Thomas J Sweet
*Assistant Examiner* — Seema Mathew
(74) *Attorney, Agent, or Firm* — Leydig, Voit & Mayer, LLP

(57) ABSTRACT

Radio-opaque endoprosthesis An endoprosthesis furnished with an armature made of metal wires visible in X-ray medical imaging in which the armature is formed of at least two layers of wires, the wires forming the armature comprising a core made of a radio-opaque material, the interaction between the cores of the wires of the various layers improving the visibility of the said endoprosthesis in X-ray medical imaging.

14 Claims, 3 Drawing Sheets

| N° | #100 | #50 | #25 | #20 | #15 | #10 | #5 | #4 | #3 | #2 | #1 | |
|---|---|---|---|---|---|---|---|---|---|---|---|---|
| Diameter (mm) | .25 | .18 | .127 | .114 | .098 | .080 | .057 | .051 | .044 | .036 | .025 | <.025 |
| Diameter (1/10 inches) | .100 | .071 | .050 | .045 | .040 | .032 | .023 | .020 | .017 | .014 | .010 | <.010 |
| Relative visibility coefficient | 100 | 50 | 25 | 20 | 15 | 10 | 5 | 4 | 3 | 2 | 1 | 0 |

Fig 2

RADIO-OPAQUE ENDOPROSTHESIS

FIELD OF THE INVENTION

The invention pertains to endoprostheses furnished with an armature whose visibility is improved in medical imaging.

TECHNICAL BACKGROUND OF THE INVENTION

The technique consisting in placing luminal endoprostheses and in particular stents in blood vessels affected by thromboses or on which aneurysms are developing is currently well known and widely applied, in particular in the cardio-vascular field.

However there is still a significant problem during placement and during subsequent checks on the state of patients: because of their slenderness, these endoprostheses are extremely difficult to pinpoint by X-ray endoscopy. The only part which appears under imaging is their armature, whose mass and thickness decrease with the diameter of the vessels treated.

The most striking case is that of interventions in the volume of the cranial box: the bones of the cranium constitute by themselves a significant obstacle for the absorption of radiation. Stents for the treatment of cerebral aneurysms are characterized moreover by their small diameter, in general of the order of 3 to 5 mm. The wires forming these stents are themselves extremely slender (of the order of 40 to 50 µm), so that it is possible to introduce the stent via a catheter whose outside diameter does not exceed 3 units French. When depositing a stent of this order of dimensions under X-ray monitoring, the stent, on account of the small thickness of the wires used and of the loss of contrast due to the thickness of the cranial box, is practically impossible to pinpoint, which means that the operator, for these very tricky operations, must work practically blind.

In practice, it is considered that most wires lose their radio-opacity for a thickness of the order of 0.1 mm. The use of noble metals (wires made of platinum, gold or tantalum) would make it possible to go down as regards visibility to a diameter of the order of 25 µm. Unfortunately, the mechanical properties of these metals are mediocre, so that it is not possible to use them alone: it is compulsory to associate them with other more resistant metals.

To alleviate this problem, various attempts have been formulated. U.S. Pat. No. 6,569,194 for example proposes the use of an alloy incorporating a metal such as tungsten, thereby obviously altering the mechanical performance of the armature.

US 2003/0121148 and WO 2005/028014 envisage, for stents formed on the basis of tubes sectioned by laser, the fixing, by welding, of inlays made of highly absorbent materials, such as platinum, gold or tantalum which therefore function as markers. This procedure makes it necessary to resort, during manufacture, to a very elaborate and expensive rig. The fixing of these inlays may possibly have to be done in two steps, since it is necessary to resort to an intermediate so-called priming layer to obtain sufficient adhesion. Furthermore, the excess material must be eliminated by electropolishing. Another problem which is related to this technique is the occurrence of galvanic corrosion phenomena between the welded material and the metal of the armature in the blood medium, acting as an electrolyte. The same problem appears in EP-0894481, where bits of radio-opaque metal wires are placed as markers on the armature.

SUMMARY OF THE INVENTION

An object of the invention is to render the armature of an endoprosthesis visible in medical imaging, without using significant quantities of radio-opaque metals, the price of which is very high and the mechanical qualities of which are mediocre.

Another object of the invention is to avoid causing problems of galvanic corrosion.

Another object of the invention is to allow the use of such an endoprosthesis in vessels of very small diameter, especially in limit contrast conditions, typically for intra-cerebral operations.

The subject of the invention is an endoprosthesis furnished with an armature made of metal wires, and typically a stent.

The endoprosthesis according to the invention is characterized in that its armature is formed of at least two layers of wires (preferably at least three layers of wires) and the wires forming the armature comprise a core made of a radio-opaque material termed an "absorber"; these at least two layers of wires, viewed laterally, take the form of a three-dimensional stack of superposed windows mutually offset in space and offer, in perspective, the appearance of a series of pyramidal frusta. The interaction between the cores of the wires of the various layers improves the visibility of the said endoprosthesis in X-ray medical imaging.

An unexpected advantage of this design is that it is possible to use very small quantities of radio-opaque material termed "absorber" while retaining visibility of surprising quality, as will be shown hereafter.

Another object of the invention is to limit to the maximum the mutual relative movements of the various layers of the armature.

To this end, the wires forming the at least two layers are preferably mutually intertwined, so that each wire forms part of each of the layers.

According to an advantageous embodiment, the diameter of the core of the wires does not exceed 25 µm, and preferably does not exceed 13 µm.

The radio-opaque material of the core is chosen advantageously within the following set [gold, platinum, tantalum].

The metal surrounding the radio-opaque core is chosen preferably within the following set [stainless steel, Elgiloy, nickel alloys, titanium alloys].

The metal surrounding the core is advantageously a shape memory material.

According to an advantageous embodiment, the wires are produced by co-extrusion.

According to a particular embodiment, the armature is devoid of coating. In this case, the endoprosthesis forms what is called a "stent".

In the description which follows, the term stent or endoprosthesis will be used interchangeably, without the use of one or the other of these terms entailing any limitation whatsoever to a particular embodiment, unless explicitly indicated.

BRIEF DESCRIPTION OF THE DRAWINGS

These aspects as well as other aspects of the invention will be clarified in the detailed description of particular embodiments of the invention, reference being made to the appended drawings, in which:

FIG. 2 is a table placing in parallel various diameters of wires consisting of a radio-opaque material and the corresponding "visibility coefficients";

The figures are not drawn to scale. Generally, similar elements are denoted by similar references in the figures.

DETAILED DESCRIPTION OF THE INVENTION

Radiopacity manifests itself by the attenuation of X-rays, during their passage through the substance. Within the framework of the invention, we shall of course speak here of X-rays only for energy levels compatible with use in medical imaging. The proportion of X-rays stopped by the substance as they pass through actually conditions the grey contrast level visible on the image.

The intensity of the rays reduces as they pass through the substance because photons may be stopped in the direction of propagation by a so-called photoelectric effect.

The decay of the intensity obeys an exponential attenuation law which is defined in the form: $I_x = I_0 \ e^{-\mu d}$ where $I_0$ is the intensity of the incident X-ray beam and $I_x$ the intensity of the absorbed beam at a distance d and μ is the linear attenuation coefficient in $cm^{-1}$ (this implies that part of the energy only is absorbed). The global attenuation of the X-ray beam is responsible for the global darkening (or brightness) of the radiographic image.

The attenuation of X-rays depends on the thickness of the object or the material, its density, the atomic number of the atoms of the component and the energy of the X-rays.

It should be noted that the greater the energy of the rays, the smaller the attenuation, and the more penetrating the rays.

Figure 1:
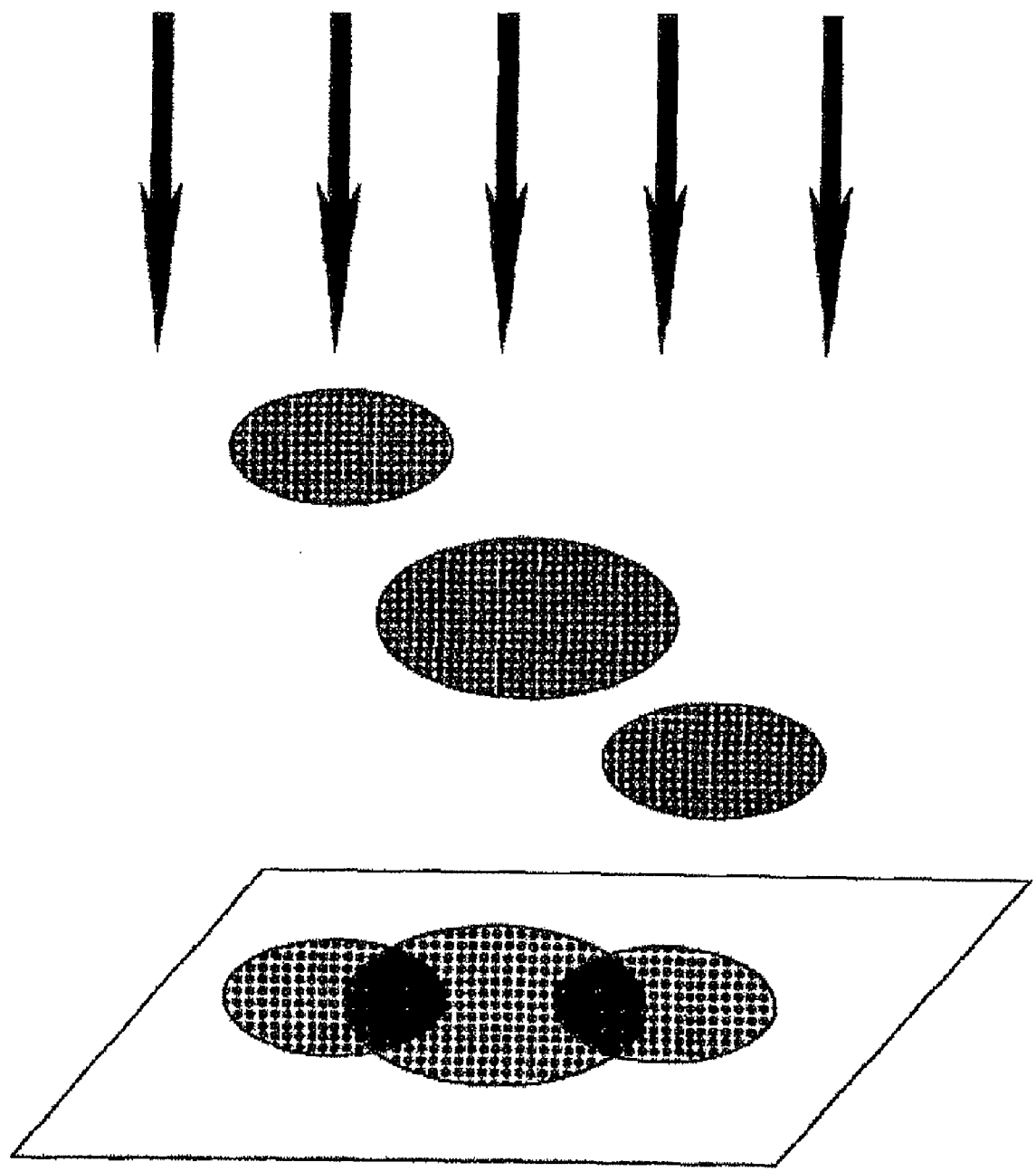
FIG. 1 is a diagrammatic view of the optical principle of imaging.

The radiographic image will therefore be formed by the differences of attenuation or of absorption of an X-ray beam as a function of the media crossed. The grey level visible in each zone of the film corresponds to the sum of the elementary attenuations produced by the obstacles (bones, muscle masses, walls of the vessels, armature of stents) successively crossed. The "shadows" of these obstacles thus appear superposed one above another without it being possible to differentiate them (FIG. 1).

Principle of the Stoppage of X-Rays

A so-called photoelectric effect occurs when an X-ray passes in proximity to an electron of a deep layer of an atom with sufficient energy to be able to eject it.

The X-ray is absorbed and the resulting energy jump is transformed into a "photoelectron" of corresponding kinetic energy. The "hole" left by the ejected electron is filled in by the jumping of an electron from a layer further out, which in its turn allows a characteristic ray $X_1$ of low energy to escape by changing orbit.

The energy of the ray $X_1$ can be regarded here as negligible, being of too weak a level to exert a significant effect on the image obtained.

The probability of interaction by a photoelectric effect is proportional to the density of the substance and to the cube of the atomic number of the constituent atoms. Atoms of high atomic number, like platinum (Z=78) or lead (Z=82) stop X-rays more easily by a photoelectric effect than atoms of low atomic number (carbon, hydrogen, oxygen, nitrogen) making up organic matter. For example, the probability of interaction by a photoelectric effect is $(78/16)^3 = 11.5$ times as large for a platinum atom (Z=78) as for an oxygen atom (Z=16).

It is considered that the photoelectric effect is the predominant effect for voltages between 50 and 70 kV.

Logic would therefore suggest the use of stents comprising significant quantities of metals of high atomic number.

This "logic" is however impossible to apply as such in medical imaging. It is firstly necessary for these materials to be medically compatible with indeterminate residence times in the human body, thereby excluding from the outset materials such as lead, uranium, etc. As regards "noble" materials, gold, platinum, tantalum, their price excludes the possibility of using them in large quantities and their implementation in an armature is difficult.

Moreover, if one desires to work on extremely fine vessels, the volume of the endoprosthesis itself begins to pose a problem. One is therefore compelled to use an armature formed on the basis of such a reduced quantity of metal that the resulting image becomes unusable, a fortiori when the background noise is significant (presence of bone), a typical situation when working in the cerebral field.

It should moreover not be forgotten that this armature, as small as it is, is intended to assume a fundamental role in the function of the endoprosthesis: to support the vessel wall into which it is inserted. Accordingly, it is necessary to resort to metals exhibiting good mechanical qualities (elasticity, bending resistance, etc.), and this does not necessarily go together with a high atomic number.

Many researchers have attempted to associate a radio-opaque metal with a core made of metal exhibiting better mechanical qualities. Cladding is, in this regard, one of the most common solutions, in particular since the quantity of "noble" metal used can be dosed in a precise manner. Unfortunately, the association of two metals bathing in body fluids gives rise to the occurrence of galvanic reactions, which eventually cause the outright dissolution of one of the metals in contact.

Within the framework of the invention, thought has therefore been given to the use of braided armatures, in preference to sectioned tubular armatures, the radio-opaque metal serving as "marker" being embedded in the wires made of more resistant material, this being possible for example by using the technique of co-extrusion.

In the case of concern to us, it is apparent that it is judicious to couple the metal wire with a powerful X-ray absorber such as platinum. A tube made of Nitinol is 30% coextruded with a platinum core and thereafter drawn to the desired diameter. This wire is supplied by Fort Wayne Metal under the name Nitinol-DFT® (Drawn Filled Nitinol Tube).

If a Nitinol-DFT® wire 40 μm in diameter is filled with 30% of platinum, the diameter of the platinum body is around 22 μm. In practice it is estimated, for the most powerful absorbents such as gold or platinum, that the value of 22 μm constitutes the lower limit of X-ray detection.

FIG. 2 is a table placing in parallel the relative visibility coefficients of platinum wires of increasing diameters. As may be seen in this table, the lower limit is attained for a wire diameter of 0.025 mm. Below this value, the signal generated is confused with the background noise of the medical imaging apparatus. Once again, one comes up against the problem of the practical limit of detection.

However, stents for the treatment of cerebral aneurysms are characterized by their small diameter, in general of the order of 3-5 mm. The wires of the stent must therefore be sufficiently fine (of the order of 40 to 50 μm) to be able to be introduced via a catheter whose outside diameter does not exceed 3 Fr (French).

According to the attenuation law mentioned above, the thickness of the material crossed is a significant factor: the thicker the material the more significant the absorption. We have had the idea of resorting to an armature formed of several successive meshed layers of material, so as to verify whether an "accumulation" of successive meshed layers could play the same role as a thick continuous layer of radiopaque material.

In the case of an armature or of a braided stent, this effect is easy to obtain by using a multilayer braiding technique, such as described in the application (PCT/BE01/00210) from the same inventor.

In the case of concern to us, it is apparent that it is judicious to couple the metal wire with a powerful X-ray absorber such as platinum. A platinum wire is inserted into a tube made of Nitinol (the wire representing 30% of the cross-section of the tube), the whole is thereafter drawn to the desired diameter. This wire is supplied by Fort Wayne Métal under the name Nitinol-DFT ® (Drawn Filled Nitinol Tube).

If a Nitinol-DFT® wire 40 µm in diameter is filled with 30% of platinum, the diameter of the platinum core is around 22 µm. As indicated above, in practice it is estimated, for the most powerful absorbents such as gold or platinum, that the value of 22 µm constitutes the lower limit of X-ray detection.

Figure 3:
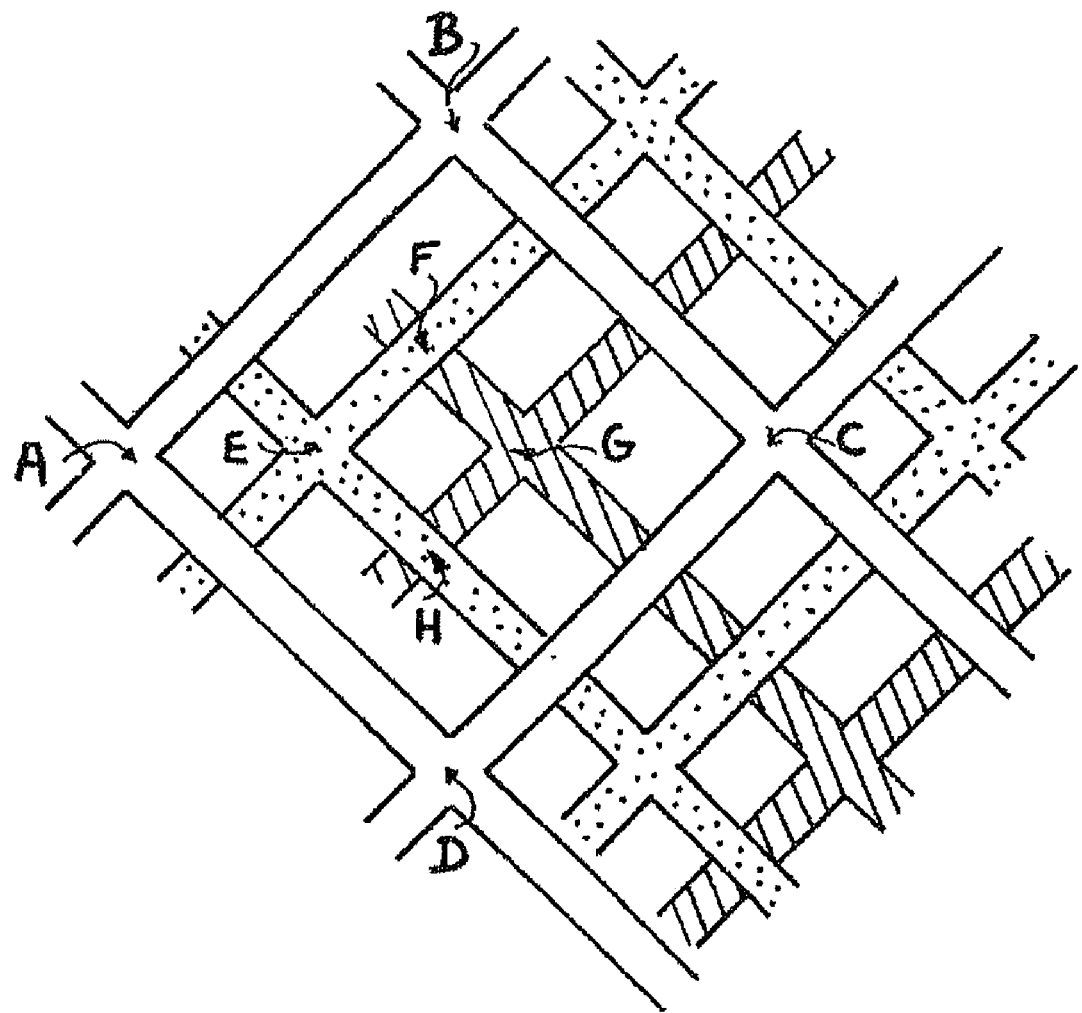
FIG. 3 is a view in close-up of a multilayer stent mesh.

As we have to do with a mesh and not with a continuous metal plate, the quantity of platinum employed is unimportant. Nevertheless, an unexpected phenomenon makes its appearance. In spite of the small quantities of metal that are involved, the global radiopacity of the stent is considerably augmented or amplified. This phenomenon can be explained as follows:

Referring to FIG. 3, it is noted that an armature with several layers—three, in this instance—viewed laterally takes the form of a three-dimensional superposition of windows superposed in space. For the sake of clarity, the intertwinings have not been represented; the mesh cells of each layer therefore appear as hollowed-out quadrilaterals.

The outermost layer is represented white, the intermediate layer is dotted, the innermost layer is hatched.

These windows being mutually offset, they offer, in perspective, the appearance of a series of pyramidal frusta.

The space between the wires of an inner layer of the stent (EFGH) appears indeed as "smaller" than the space between the wires of an outer layer (ABCD). This phenomenon appears all the more marked as the number of layers grows. The mesh cells of the elementary quadrilaterals of each wall are superposed one below another to infinity, forming cones whose base (ABCD) coincides with the outermost layer of the armature.

A stream of X-rays emitted by the source used by a medical imaging apparatus encounters the surface of the stent at a given angle of incidence. The platinum core of each wire will absorb about 78% of the rays. The nonabsorbed part, instead of scattering or being absorbed by the bones or the tissues surrounding, is absorbed gradually by the neighbouring wires.

This successive arrangement of layers exhibiting wires of the same orientation offers the advantage that the scattered X-rays, the secondary X-rays and the rays not absorbed by bone and tissues are kept for all angles of incidence. A stent of such a configuration therefore plays the role of an anti-scatter grid. This phenomenon increases with the number of layers that are piled up, from two layers on.

The reality of this phenomenon is backed up by the following 2 experiments.

EXAMPLE 1

It is indicated above that the lower limit thickness for the most absorbent metals is 22 µm. It transpires that the supplier has available a 44 µm DFT wire with 10% of platinum, this giving a platinum thickness of 13 µm.

A stent formed of a braid, as described above, embodied with this wire produces during trials a fully visible and more contrasted image on the bone and the tissues surrounding than the control stent.

EXAMPLE 2

A single-wall stent, braided with a wire 40 µm in diameter containing 30% of platinum admittedly demonstrates radiopacity to X-rays, but as soon as it is placed in a bony environment, it is no longer visually discernable.

This example shows that the bone absorbs all the lost and nonabsorbed rays in the vicinity of the stent, thereby increasing the background noise due to bone. Such a phenomenon is absent in the case of a single-wall stent.

Effect on Aneurysms

The effect described above can be obtained by placing several stents (or endoprostheses) of corresponding diameters one inside another, but this is a rather impractical procedure, in particular on account of the difficulty of alignment of these stents (or endoprostheses) and of a possible migration problem (relative displacement of each of the stents with respect to the wall of a blood vessel). Trials show that a far better result is obtained with a single multilayer braided stent.

A problem that one seeks to solve with the fitting of endoprostheses or of cerebral stents is that of forestalling the development of aneurysms, rupture of which engenders effects that are frequently fatal for the patient.

Cerebral aneurysms are classed according to their size, which takes into account at one and the same time the diameter of the aneurysmal sac but also the width of the neck (passage between the aneurysmal sac and the blood vessel on which the aneurysm develops). They are classified differently according to author. Higashida, for example, classifies aneurysms into 3 categories, aneurysms of "small to average" size when the pocket remains less than 12 mm, "wide" aneurysms from 12 to 25 mm and "giant" aneurysms greater than 25 mm.

Treating cerebral aneurysms is generally done by routing a "coil" placed in the pocket of the aneurysm to seal it off. The current state of the art shows that this treatment can be effective for aneurysms with a small neck (2 to 3 mm), given that the size of these aneurysms can vary, and especially grow.

Most aneurysms in fact exhibit a neck whose size exceeds 4 mm; "coil"-based treatment of these so-called giant aneurysms does not make it possible to treat them effectively: In a goodly number of cases, the practitioner is required to fit several "coils" without the aneurysm thrombosing successfully. A pernicious phenomenon can moreover occur: the migration of these coils towards the main artery. To avoid this problem, some practitioners previously place in the artery, in line with the neck of the aneurysm, a stent assuming the function of a non-return device, generally a cylinder made of Nitinol sectioned by laser so as to form wide mesh cells. They thereafter insert one or more coils into the aneurysm through the mesh cells of the stent, the latter preventing a subsequent return of the coil towards the artery. This method, with several steps, gives rise to a lengthy, irksome and expensive procedure, for a high failure rate.

Particular Features of Treatment by Double-Wall Stent

The entry of blood into a saccular aneurysm occurs through the upper part of the neck (distal with respect to the arrival of the stream); the stream engendered creates a whirlpool (vortex) which moves along the entire saccular wall until its exit. This vortex is followed by another, then by another, which, in time with the beating of the heart, follow one another in a continuous manner. The fact that these vortices do not follow strictly the same trajectory in the aneurysm creates a disturbance (whirlpooling) which maintains the pressure against the wall of the aneurysmal sac, which narrows gradually by dilating, doing so until possible rupture.

We have sought to modify this haemodynamics in the aneurysm by disabling the motion of these whirlpools, thereby favouring the stagnation of the blood and consequently coagulation (thrombosis) in the actual pocket of the aneurysm.

Various attempts have been made to create this thrombosis by placing a conventional endoprosthesis or stent (cylinder sectioned by laser, with dilation by balloon or monolayer braid) at the entrance of the aneurysm.

It has turned out that on the one hand stents have not produced the positive effect hoped for (in the sense of the induction of a thrombosis) on the incoming blood stream. On analysis, in regard to the surface area of the neck, their meshing represents a very small surface area of coverage (projection of the mesh cells onto the plane of the neck). The ratio [surface area of the neck/surface area occupied by the mesh cells] is therefore small. Increasing this ratio would pose a bulkiness problem in the fitted catheter, resulting in increased difficulty of insertion and of navigation in the cerebral arteries, which are by nature particularly tortuous.

For their part, endoprostheses consisting of a rigid armature covered with a film (of polyester or PTFE) pose problems of bulkiness and of inflammatory reactions related to the polymer molecules.

On the other hand, it is found that the configuration proposed by the invention, i.e. generally a multilayer braid where the various layers are superposed one on top of the other and mutually offset, affords the stent used a significant role in the alteration of the stream, which finally stagnates, favouring haemostasis which essentially involves the blood platelets (thrombocytes). This finding is a priori entirely paradoxical, since, the wires being finer, the coverage [surface area of the neck/surface area occupied by the mesh cells] is of the same order as previously.

In order to close the aneurysm effectively on one side and ensure the permeability of the branches which may be located opposite the aneurysm or a few millimeters upstream and downstream of it, we have used a stent of porosity equivalent to that of a monolayer stent (that is to say 70 to 80%) but using a different three-dimensional arrangement of the pores and the layers so as to obtain a lower permeability, sufficient to attenuate the force that the vortices create when forming immediately upon entry into the aneurysm. The permeability to water is defined as the quantity of water (in $gr/min \cdot cm^2$) passing into a standardized apparatus under a pressure corresponding to 120 mmHg). In this instance, without the stent it is 14 260 $gr/min \cdot cm^2$ (i.e. 100%) and with a 3 mm stent is of the order of 12 162±76 $gr/min \cdot cm^2$, i.e. 85%.

The porosity is therefore objectively of the same order of magnitude as that of a monolayer stent (for example of the type of a tube sectioned by laser, or braided). What renders the multilayer stent more effective, is therefore the way in which the mesh cells are distributed in space, stated otherwise, it is the modification of the three-dimensional geometry which dictates the effectiveness of the stent in altering the haemodynamics and, accordingly, thrombosing the aneurysm.

Another advantage exhibited by the stent of the invention over endoprostheses covered with a film will be noted: frequently aneurysms are situated in proximity to collateral vessel branch-offs in a blood vessel. When this is the case, the placement of a covered endoprosthesis runs the risk of sealing off not only the aneurysm, but also these collateral vessel branch-offs. Such a phenomenon cannot occur with an uncovered stent, through which the blood stream passes without any problem.

Moreover, the braiding allows the stent to adopt a minimum cross-section during its introduction (under reduced diameter) into a catheter.

A last, and no lesser, effect was noted by checking a posteriori via in-vivo assessments the progress of the restenosis (blood platelet accumulation) on the walls of a vessel covered internally by a stent or an endoprosthesis. By an as yet hitherto unexplained effect, but which could be related to the reciprocal rubbing of the wires forming the various layers of the armature, a surprising absence of restenosis is noted. The multilayer braid would therefore have an unexpected "self-cleaning" function, thereby opening up prospective new applications for this type of stent.

It will be evident to the person skilled in the art that the present invention is not limited to the examples illustrated and described above. The invention comprises each of the new characteristics as well as their combination. The presence of reference numbers cannot be regarded as limiting. The use of the term "comprises" can in no way exclude the presence of other elements other than those mentioned. The use of the definite article "a" to introduce an element does not exclude the presence of a plurality of these elements. The present invention has been described in conjunction with specific embodiments, which have a purely illustrative value and shall not be regarded as limiting.

The invention claimed is:

1. Endoprosthesis furnished with an armature made of metal wires, the wires forming the armature, each wire comprising a core made of a radiopaque material, wherein;
   the armature is formed of at least two layers of wires;
   these at least two layers of wires, viewed laterally, take the form of a three-dimensional stack of superposed windows mutually offset in space and offer, in perspective, the appearance of a series of pyramidal frusta, and
   the diameter of the core of a wire does not exceed 13 µm, the interaction between the cores of the wires of the various layers causes said endoprosthesis to be visible in X-ray medical imaging.

2. Endoprosthesis according to claim 1, wherein the armature is formed of at least three layers of wires.

3. Endoprosthesis according to claim 1, wherein the wires forming the at least two layers are mutually intertwined, so that each wire forms part of each of the layers.

4. Endoprosthesis according to claim 2, wherein-the wires forming the at least three layers are mutually intertwined, so that each wire forms part of each of the layers.

5. Endoprosthesis according to claim 1, wherein the radio-opaque material of the core is selected from the group consisting of gold, platinum, and tantalum.

6. Endoprosthesis according to claim 3, wherein the radio-opaque material of the core is selected from the group consisting of gold, platinum, and tantalum.

7. Endoprosthesis according to claim 1, wherein the metal surrounding the radio-opaque core is stainless steel, Elgiloy, nickel alloys, and titanium alloys.

8. Endoprosthesis according to claim 7, wherein the metal surrounding the core is a shape memory material.

9. Endoprosthesis according to claim 1, wherein the wires are produced by co-extrusion.

10. Endoprosthesis according to claim 3, wherein the wires are produced by co-extrusion.

11. Endoprosthesis according to claim 1, wherein the armature is devoid of coating.

12. An endoprosthesis having an armature made of a plurality of metal wires, the wires forming the armature, with each wire comprising a core made of a radiopaque material,
wherein the armature includes at least two layers of wires, which when viewed laterally, take the form of a three-dimensional stack of superposed windows mutually offset in space and offer, in perspective, the appearance of a series of pyramidal frusta, and
wherein the diameter of the core of a wire does not exceed 25 μm, whereby the interaction between the cores of the wires of the various layers causes the endoprosthesis to be visible in X-ray medical imaging.

13. The endoprosthesis of claim 12, wherein the diameter of the core of each wire does not exceed 13 μm.

14. An endoprosthesis, comprising:
a first layer of metal wires; and
a second layer of metal wires,
wherein the second layer of metal wires is stacked on the first layer of metal wires in a position that is laterally offset relative to a position of the first layer of metal wires,
wherein each wire included in the first layer of metal wires and each wire included in the second layer of metal wires includes a core made of radiopaque material that has a diameter that does not exceed 13 μm, and
wherein the endoprosthesis is visible in X-ray medical imaging based on the cores of the wires of the first layer of metal wires and the cores of the wires of the second layer of metal wires appearing as a series of pyramidal frusta.

* * * * *